United States Patent
Collasius et al.

(10) Patent No.: US 6,959,836 B2
(45) Date of Patent: Nov. 1, 2005

(54) DISPENSER

(75) Inventors: Michael Collasius, Hombrechtikon (CH); Konstantin Lutze, Hombrechtikon (CH); Pius Fink, Hombrechtikon (CH); Marco Di Berardino, Stäfa (CH)

(73) Assignee: Qiagen-GmbH, Hilden (DE)

( * ) Notice: Subject to any disclaimer, the term of this patent is extended or adjusted under 35 U.S.C. 154(b) by 0 days.

(21) Appl. No.: 10/204,574
(22) PCT Filed: Feb. 19, 2001
(86) PCT No.: PCT/EP01/01855
§ 371 (c)(1), (2), (4) Date: Feb. 6, 2003
(87) PCT Pub. No.: WO01/62388
PCT Pub. Date: Aug. 30, 2001

(65) Prior Publication Data
US 2003/0155371 A1 Aug. 21, 2003

(30) Foreign Application Priority Data
Feb. 22, 2000 (DE) .......................... 100 08 003

(51) Int. Cl.⁷ ................................ G01F 11/00
(52) U.S. Cl. ................ 222/1; 222/63; 222/72; 222/318; 222/397
(58) Field of Search ............... 222/1, 63, 72, 222/73, 318, 383.1, 397, 504

(56) References Cited

U.S. PATENT DOCUMENTS

| | | | |
|---|---|---|---|
| 1,286,976 A | * 12/1918 | Farr | 222/72 |
| 3,958,724 A | 5/1976 | Ordway | 222/318 |
| 4,023,709 A | * 5/1977 | Becker et al. | 222/638 |
| 4,028,441 A | * 6/1977 | Richards | 261/36.1 |
| 4,106,699 A | 8/1978 | Holt | 239/124 |
| 4,787,822 A | 11/1988 | Bennett | 417/2 |
| 5,589,077 A | 12/1996 | Matsuda et al. | 210/741 |
| 5,823,388 A | 10/1998 | Green | 222/1 |
| 6,179,163 B1 | * 1/2001 | Bohr et al. | 222/72 |

FOREIGN PATENT DOCUMENTS

| | | |
|---|---|---|
| DE | 196 49 888 | 6/1998 |
| EP | 0 283 137 | 9/1988 |
| EP | 0 645 564 | 3/1995 |
| EP | 0 690 294 | 1/1996 |
| WO | WO 00/02047 | 1/2000 |

* cited by examiner

Primary Examiner—Joseph A. Kaufman
(74) Attorney, Agent, or Firm—Yankwich & Associates, P.C.; Leon R. Yankwich; Michael R. Wesolowski (57) ABSTRACT

The invention relates to a dispensing device and a method for dispensing liquids, preferably reagents, in an essentially automated and finely dosed manner. The dispensing device comprises a first duct that is connected to a storage element for storing the liquid to be dispensed. In addition, a conveying element for conveying the liquid through the fist duct is provided, whereby the liquid has to be dispensed. Liquid is transported from the storage element and is conveyed into the first duct by the conveying element. Moreover, the dispensing device is provided with a closing device that is arranged downstream in the conveying direction of the liquid in relation to the conveying element and serves for quickly closing and quickly opening the first duct. The aim of the invention is to regulate the pressure of the liquid in the region between the conveying element and the closing device. A device for regulating the pressure of the liquid in this region is provided. Liquids can be very exactly and repeatedly dispensed in short time intervals by means of the inventive device and the inventive method. In another embodiment of the invention, a dispensing element is provided for evenly dividing the liquid stream into partial streams.

38 Claims, 8 Drawing Sheets

DISPENSER

This application is a United States national filing under 35 U.S.C. §371 of international (PCT) application No. PCT/EP01/01855, filed Feb. 19, 2001, claiming priority to EP Application No. 100 08 003.0.

TECHNICAL FIELD

The invention relates to apparatus and processes for the automatic and finely metered dispensing of liquids. It additionally relates to a dispensing element for use in a dispenser or in a dispensing process.

BACKGROUND OF THE INVENTION

In many technical fields it is necessary to measure out precise amounts of one or more liquids and then supply them for a particular application. In the fields of chemistry and biotechnology, in particular, it frequently happens that one of several steps of a process in a reaction comprises measuring out finely metered amounts of a liquid and supplying them to the reaction. The term liquid here basically means any chemical substance which is present in liquid form.

The measuring out and supplying of liquids may be done manually using pipettes or with other intermediate storage elements. However, such manual proceedings require an operator and are also usually very time-consuming. For this reason the manual measuring out and supplying of liquids is usually only used at the experimental stage or for very low repeat rates. In applications where the repeat rate is very high or where very uniform measurement and supplying of one or more liquids is required, possibly at identical times, attempts are usually made to automate the process. Thus, for example, the "Biorobot 9600" system produced by the present applicant has been on the market for some years for carrying out molecular-biological processes such as the washing and extraction of nucleic acids or the isolation of RNA and/or DNA.

Thus, in order to produce highly purified DNA plasmids, a number of steps are carried out one after another, the individual steps being carried out at different, precisely fixed intervals of time relative to one another. First of all, cell cultures are placed in containers such as individual or multiple test tubes using an individual pipetting device. The cell cultures are put back into suspension and lysed. Then the cell cultures in solution are transferred into other containers using the pipetting apparatus. This is usually followed by filtration to purify the lysates. Filtering is carried out using special containers which have suitable filter elements set into their bases. A vacuum can be applied to the containers through an opening in the underside of the containers, through which the solution is sucked through the filters and thus filtered. Alternatively, the samples may also be centrifuged to separate them in a conventional but time-consuming manner. After the filtering, the DNA is adsorbed by means of a suitable membrane in another step. The DNA-free solution remaining can be removed by a rinsing process. The desired DNA is then recovered by a subsequent elution step.

The dispensers known from the prior art are generally in the form of individual dispensers, so that the measuring out and supplying of a liquid to a plurality of containers can only be carried out sequentially, i.e. one after another. The measuring device itself usually consists of a flexible tube in which a liquid pressure is built up using a pump. Just in front of the outlet from the flexible tube there is generally a valve which is briefly opened as required. The quantity of liquid flowing through the valve is accordingly directly dependent on the preliminary pressure prevailing in the flexible tube. Particularly if the valve is opened frequently at different time intervals, depending on the pump power between the individual valve opening processes, the pressure is not built up completely to the nominal pressure. Accordingly, the preliminary pressure prevailing in the line fluctuates substantially in some cases, with the result that uneven amounts of liquid are dispensed.

DESCRIPTION OF THE INVENTION

The invention is therefore based on the problem of providing apparatus and processes for the automated and finely metered dispensing of liquids and a dispensing element which can be used in an apparatus according to the invention, with the intention of largely overcoming the problems known from the prior art. In particular, with the aid of the invention, a constant amount of liquid should be delivered each time, even when the dispensing process has a high repeat rate, and the dispensing processes may also take place at different time intervals from one another.

Further advantages, features, aspects and details of the invention will become apparent from the claims, the specification and the accompanying drawings. The invention is not restricted to the contents of the claims.

According to a first aspect of the invention the objective described above is achieved by means of a dispenser constructed according to the invention for the substantially automated and finely metered dispensing of liquids, preferably reagents. For this purpose the dispenser comprises a first line which may be connected to a storage element, e.g. a storage bottle, to store the liquid which is to be dispensed.

Moreover, the dispensing device comprises a conveying element for conveying the liquid which is to be dispensed through the first line. The liquid is sucked out of the storage element by means of the conveying element and conveyed into the first line. A closure device for rapid closure and rapid opening of the first line, preferably a solenoid, is also mounted downstream of the conveying element in the direction of conveying of the liquid. Preferably, the closure device is arranged at a short distance from the end of the second line or actually at the end of the second line.

In the region between the conveying element and the closure device there is also preferably a device for regulating the pressure of the liquid. The conveying element, usually a pump, preferably a diaphragm pump, preferably conveys liquid continuously from the storage element into the first line throughout the dispensing process. For this purpose the conveying element is advisably but not necessarily connected to the storage element, e.g. a storage bottle, which contains the liquid to be dispensed, by a second line. If the closure device is in the closed position, i.e. if the closure device is closing off the first line and thus preventing the liquid from flowing out of the first line, there is a buildup of liquid in the region between the conveying element and the closure device. By means of the device for regulating the pressure of the liquid, which in the simplest case is constructed as a pressure relief valve, preferably with recycling of the liquid, the pressure is limited to a threshold value in the region between the conveying element and the closure device. If the closure device is now briefly opened, a defined amount of liquid flows out into the region behind the closure device, depending on the period of opening of the closure device, the supply pressure, i.e. the pressure of the liquid in the region of the first line between the conveying element and the closure device, and the flow resistance of the current of liquid. From here the liquid can expediently be conveyed to its intended destination via a distributor head or an individual pipetting device.

If the volume of the pipe section between the conveying element and the closure device is large enough and it thus acts as a pressure storage space, and/or if the conveying element has a sufficiently high conveying power, the outflow of liquid may result in only a very slight drop in pressure of the liquid in the pressure storage space. For practical purposes it can be assumed as a reasonable approximation that a constant supply pressure will prevail in the pressure storage space over time. If the closure device is opened repeatedly at short intervals, in spite of the repeated delivery of liquid with an extremely limited range of fluctuation the same amount of liquid will be dispensed each time. The device for regulating the pressure of the liquid ensures that the supply pressure is restricted upwardly and accordingly not too much liquid is discharged. In contrast to numerous dispensers known from the prior art, the conveying element of the dispenser constructed according to the invention may be operated continuously with a constant delivery over time. Non-linear patterns of conveying quantities, particularly when the conveying element is being lifted up or put down, are thus avoided during the dispensing process.

Preferably, an aspirating needle is provided at the end of the second line closest to the storage element. The aspirating needle is conveniently releasably connected to the second line and can thus be exchanged when necessary. In order to regulate the depth of immersion of the aspirating needle in the liquid contained in the storage element, a liquid sensor for determining and regulating the depth of immersion into the liquid in the storage element is conveniently mounted on the end of the second line closest to the storage element and/or the aspirating needle. Thus, the position of the aspirating needle can be regulated automatically as the level in the storage element falls. The moment when the aspirating needle reaches its maximum depth of immersion in the storage element can be used as a control signal for starting a preferably fully automatic exchange of the storage element or at least to emit a warning signal to alert an operator to the need to change the storage element. Preferably, the end of the second line closest to the storage element and/or the aspirating needle may be moved in the direction of immersion in the liquid in the storage element. To enable adjacent storage elements to be moved closer together or to enable the aspirating needle to be moved into a resting position or a changeover position, however, it is often also convenient to make the end of the second line which is closest to the storage element and/or the aspirating needle moveable transversely with respect to the depth of immersion in the liquid contained in the storage element.

Appropriately a dispensing element with at least one inlet opening and at least one outlet opening is provided on the second end of the first line remote from the storage element. In addition, one or more collecting containers into which the liquid is delivered are preferably provided at the exit from the first line and/or the dispensing element. Using the dispensing element, the liquid to be dispensed can be supplied in highly accurate amounts to the individual collecting containers. To prevent the liquid from dripping out of the first line and/or the dispensing element, the dispensing element is preferably provided with a sharp tear-off edge at the outlet end. Providing the smoothest possible surface on the line which extends in the dispensing element also prevents liquid from accumulating in the dispensing element. Accumulations in the dispensing elements would lead to soiling in subsequent dispensing operations or might result in fluctuations in the quantity of liquid.

The dispensing element is preferably constructed as a dispensing head which is preferably automatically moveable horizontally and/or in the vertical direction and/or about a rotation axis. The movement is preferably controlled by means of an electronic control system which preferably contains a programmable microprocessor. Thanks to the mobility of the dispensing head it is possible to move the dispensing head into an optimum position relative to the collecting container and to move it back out of this position after the dispensing process. The dispensing element may expediently be changed automatically, preferably by means of a gripper, so that different dispensing heads can be used depending on the particular application.

Preferably, the direction of conveying of the conveying element can be reversed. Thus, not only can liquid be conveyed from the storage element into the first line and preferably dispensed using the dispensing element but also liquid can be conveyed in the opposite direction from a container with which the first line preferably communicates via the dispensing element, towards the storage element.

Preferably, the moment of opening and closing of the rapid closing device is controlled by a control device, preferably a microprocessor. By means of the control device and particularly by means of a programmable microprocessor, it is possible to achieve high reproducibility of the dispensing process through the emission of control signals to the rapid closure device. Preferably, one or more input signals, e.g. indicating the fullness of the storage element, are additionally processed in the microprocessor and moreover other control means such as grippers for replacing the storage elements are actuated.

According to another aspect of the invention, a dispensing element is provided, wherein the dispensing element comprises an inlet opening and at least two outlet openings, as well as a first and a second transverse channel for distributing the liquid which is to be dispensed and at least two supply channels between the first and second transverse channels.

The provision of two transverse channels ensures that the liquid which is to be dispensed emerges uniformly from the outlet openings. It is presumed, without going into the physical basis in detail, that the transverse channels create two pressure stages by means of which the pressure prevailing at the respective outlet openings is uniformly distributed. The liquid is transported from one pressure stage to the next by means of the supply channels.

Preferably, a dispensing element has four or twelve outlet openings. It is particularly preferable to use eight outlet openings.

Preferably, the individual channel sections, e.g. the inlet channel, first transverse channel, supply channels, second transverse channel and outlet channels, are arranged perpendicularly to one another. This makes the manufacture of the dispenser easier and reduces differences in the volume dispensed. Irrespective of this the invention may also be constructed with channels extending slightly diagonally.

According to another preferred embodiment of the invention the two transverse channels extend at the same level in the dispensing element. This reduces the influence of the gradient and the natural tendency of liquid to take the shortest vertical route when allowed to flow unhindered. In this case, the outlet channels located immediately adjacent the inlet opening would tend to promote larger volumes of liquid.

In another preferred alternative embodiment the first transverse channel runs underneath the second transverse channel. The liquid is thus forced to climb counter to the gradient, starting from the first transverse channel through the supply channels into the second transverse channel. The liquid arriving in the first transverse channel through the inlet channel is thus first of all uniformly distributed in the first transverse channel and fills it before rising uniformly upward through the supply channels and filling the second transverse channel. This ensures an even pressure distribution in the second transverse channel.

In order to fill the second transverse channel, preferably N supply channels are used with 2N outlet channels. This ensures a sufficient flow of liquid with a uniform pressure distribution. It is particularly preferable for a supply channel to open into the second transverse channel at a spacing from two outlet channels. The channels are preferably arranged symmetrically. This ensures that each outlet channel is arranged outside the outermost supply channels. Other arrangements of the supply channels to the outlet channels or numerical ratios between the supply and outlet channels are also covered by the invention. Thus, for example, in a dispensing element having one inlet channel and two outlet channels it is advantageous to arrange two supply channels between the first and second transverse channels. In this arrangement the number of supply channels is equal to the number of outlet channels.

In a preferred embodiment, the dispensing element comprises two flushing channels which preferably connect the two transverse channels together outside the outermost outlet channels. The flushing channels prevent the formation of bubbles or dead spaces at both ends of the first transverse channel and thus supply the outermost outlet channels with the same amount of liquid. Preferably, the diameters of the flushing channels are smaller than the diameters of the supply channels, so as to avoid a greater throughput of liquid through the outer outlet channels compared to the outlet channels located on the inside. It is also advantageous to make the diameters of the transverse channels greater than the diameters of the supply channels.

In another advantageous embodiment the dispensing element has more than two pressure stages or transverse channels. When there is a larger number of outlet channels, in particular, e.g. if there are more than eight outlet channels, this ensures a more uniform distribution of liquid or pressure at the outlet channels. A disadvantage is that the total amount of liquid contained in the channels is increased, resulting in more waste when the liquid being dispensed is changed.

According to another aspect of the invention a dispensing element is provided particularly for use in the dispensing device described above. The dispensing element according to the invention has an inlet opening and eight outlet openings, the inlet opening being connected to the outlet openings by means of channels extending in the dispensing element, and the flow resistance along the channels between the inlet opening and each of the eight outlet openings is identical. This ensures that any liquid getting into the dispensing element through the inlet opening is distributed equally to the outlet openings. Consequently, one eighth of the liquid supplied through the inlet opening is dispensed at each of the eight outlet openings. This ensures an effecient and proportional distribution of a quantity of liquid to the eight outlet openings. In conjunction with the dispenser according to the invention described above, eight equal amounts of liquid can be dispensed into preferably eight collecting containers in one opening cycle of the closure device. Preferably, the eight collecting containers are arranged side by side for this purpose.

The channels from the inlet opening to the outlet opening are arranged according to a preferred embodiment of the dispensing element according to the invention so that a first channel which is connected to the inlet opening in the dispensing element first branches into four second channels which in turn each divide into two third channels. Each of the third channels is connected to an outlet opening. In addition, the branches of the channels in the branching plane communicate with one another. Consequently, pressure can be equalised in each branching plane, so that any unevenness of flow which may occur within the channel system can be balanced out.

It has been found that the differences between the volumes of liquid dispensed through the individual outlet openings can be reduced by larger pressure stages or transverse channels. The higher accuracy is accompanied by a larger total volume of liquid contained in the dispenser element, which has to be disposed of beforehand in other steps of the process that require changing the liquid. If the liquid is changed frequently, the large amounts of waste will require earlier changing of the storage containers. Precisely in the case of apparatus in which the storage containers are changed by hand the levels have to be monitored constantly. It is thus desirable to keep the amount of waste as low as possible. The dispenser element is designed as a compromise between a high accuracy of metering and a small total volume determined by the channels for receiving liquid. Depending on the number of outlet channels to be supplied the best design of the dispenser head is determined imperically. This relates both to the size ratios of the individual channels and to the number of channels.

Preferably, the individual channels are round. However, other shapes are also possible such as rectangular or oval, for example.

When the direction of conveying is reversed the dispensing element described may preferably be used as an aspiration tool. It is suitable for removing precisely defined quantities of liquid from individual liquid containers.

In another aspect of the invention a process for the substantially automated, finely metered dispensing of liquids, preferably reagents, is provided. The process comprises the following steps:
 sucking the liquid out of a storage element into a pipe system,
 building up pressure of liquid which is substantially constant over time in at least one section of the pipe system,
 metering the quantity of liquid which is to be dispensed by briefly opening a rapid-acting closure device provided in the pipe system, so as to dispense a quantity of liquid from the section of the pipe system corresponding to the period of opening of the rapid-acting closure device and the liquid pressure.

The process is preferably carried out using the apparatus according to the invention for dispensing liquids.

Conveniently, before the step of sucking the liquid out of a storage element, one end of the pipe system is automatically moved horizontally and/or vertically and/or in a rotary movement so that the pipe system communicates with a selected storage container.

The step of metering the liquid which is to be dispensed can be repeated several times in succession. Before each new metering process the other end of the pipe system is conveniently automatically moved horizontally and/or vertically and/or in a rotary movement so that the quantity of liquid metered is dispensed into one or more selected containers. The containers into which the metered liquid is dispensed are preferably moved horizontally and/or vertically and/or in a rotary movement in a controlled manner, before each fresh metering process, so that the containers in question are arranged in a suitable position for the metering process.

In order to build up the pressure which is constant over time, the liquid is preferably continuously conveyed by means of a pump. The pressure may be limited on the pump delivery side by pressure-controlled recycling of the liquid. Preferably, if a maximum pressure is exceeded in the pipe system, the liquid is recycled into the storage element. Alternatively, if a maximum pressure is exceeded in the pipe system, the liquid might also be recycled into a part of the pipe system situated in front of the pump.

After the dispensing of the liquid has ended the pipe system is conveniently washed with a washing liquid. This prevents any residues of a previous dispensing process being left in the pipe system and subsequently causing contamination.

The invention also relates to processes which can be carried out on or with the apparatus disclosed. It comprises steps for performing each function of the apparatus. The invention also relates to apparatus for carrying out the processes disclosed and to features of the apparatus for carrying out the steps described. These steps may be carried out using hardware components, using computers with corresponding software programs, by combinations thereof or by some other method.

BRIEF DESCRIPTION OF THE DRAWINGS

Some of the aspects of the invention described above as well as other more detailed aspects are explained more fully hereinafter and are illustrated to some extent in the accompanying drawings, which show in particular:

FIG. 3a a preferred embodiment of the dispenser according to FIG. 3;

METHODS OF PERFORMING THE INVENTION

Figure 1:
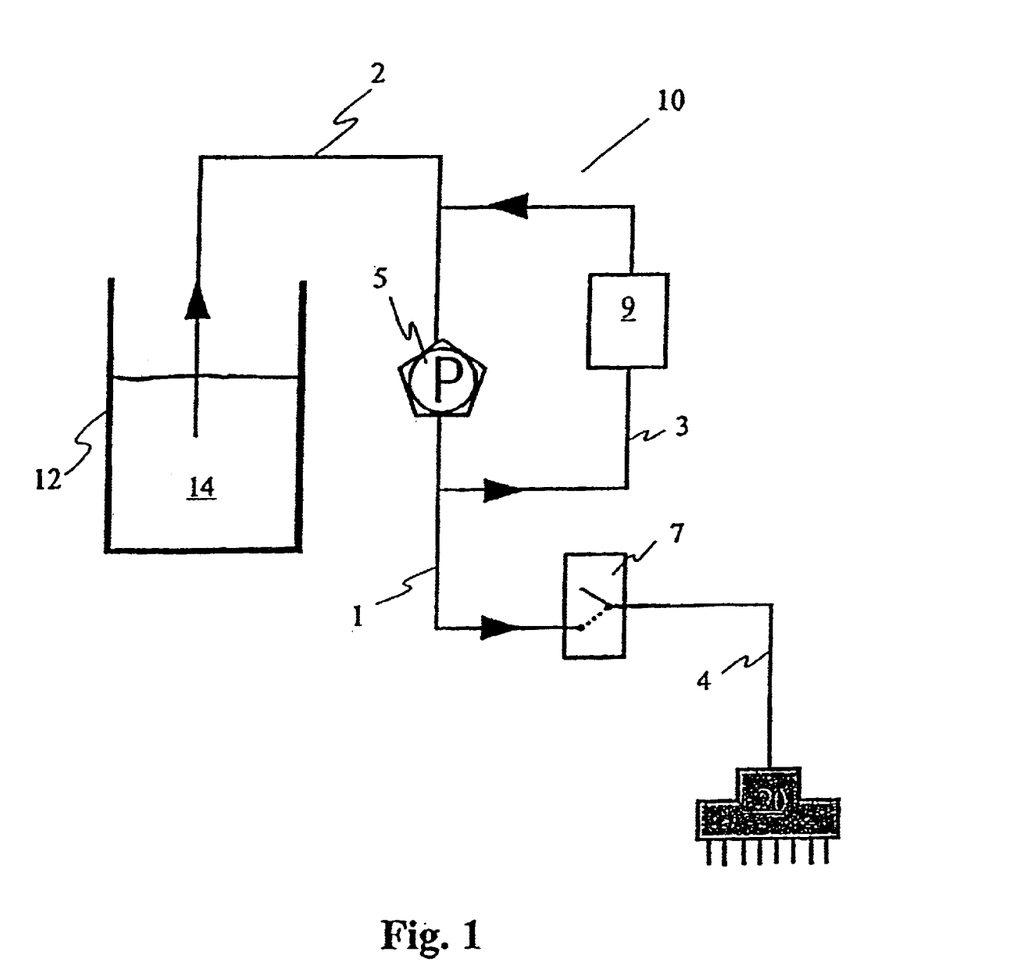
FIG. 1 a first dispenser constructed according to the invention in diagrammatic view.

The arrangement shown in FIG. 1 diagrammatically shows a first dispenser 10 constructed according to the invention. The dispenser shown here essentially comprises a first line 1, a diaphragm pump 5, a solenoid 7 and a third line 3 with a pressure maintaining valve 9 integrated in this third line. The first line is provided as a connecting element between the diaphragm pump 5 and the solenoid 7. In addition, the diaphragm pump 5 is connected on its inlet side, by means of a second line 2, to a storage element 12, in this case a buffer bottle. The buffer bottle contains a liquid 14 to be dispensed. In addition, the solenoid is connected by a fourth line 4 to a dispensing head 20, in this case an 8-channel dispensing head. The third line 3 branches off from the first line 1 in the form of a recycling line and opens into the second line 2 in front of the diaphragm pump 5. The pressure maintaining valve 9 may be constructed simply as a pressure relief valve and may preferably be switched to open when a pressure threshold is exceeded in the direction of flow from the first line 1 to the second line 2. The recycling loop comprising the third line 3 and the pressure maintaining valve 9 serve here as a device for regulating the pressure of the liquid in the first line 1.

The arrows in FIG. 1 indicate the direction of flow of the liquid which is to be dispensed within the dispenser 10. The diaphragm pump 5 continuously sucks liquid 14 out of the buffer bottle 12 through the second line 2 and conveys it into the first line 1. If the solenoid 7, which is constructed here as a 2/2-way solenoid, is closed, there is a build-up and as a result of the continuous conveying of the diaphragm pump 5 there is a rise in pressure in the liquid conveyed in the first line 1. In the case of a pressure maintaining valve 9 constructed as a pressure relief valve, the pressure relief valve opens when a threshold pressure value is reached. In a preferred embodiment of the pressure relief valve the pressure threshold may be manually selected or selected by computer control and adjusted accordingly within a preferred pressure range. When the pressure relief valve 9 opens liquid flows from the first line 1 through the third line 3 back into the second line and is thus recirculated. The arrangement shown in FIG. 1 is a particularly preferred embodiment of the invention.

The flow resistance for flow through the third line has to be selected so that with continuous conveying and the pressure maintaining valve 9 open in the first line 1 a liquid pressure is obtained which is constant over time. This may be achieved either by a suitable choice of the cross-sections of flow of the third line 3 or by means of a suitably selected, i.e. not too great, cross-section of opening of the pressure maintaining valve 9 or an additional constriction. Thus, the first line contains a quantity of liquid at a well defined pressure which is constant over time. If the 2/2-way solenoid 7 is then opened, liquid flows out of the first line 1 into the fourth line 4 and from there into the dispensing head 20. In the dispensing head 20 the incoming flow of liquid is divided up into eight equal parts and supplied to the eight outlet openings 24. Finally, the liquid flows through the eight outlet openings 24 and through aspirating needles of the dispenser 10 which are provided at the outlet openings.

Conveniently, but not shown in FIG. 1, collecting containers such as a microtitre plate, into which the liquid is dispensed and which can preferably be changed over automatically, are provided at the exit from the aspirating needles. The duration of opening of the 2/2-way solenoid 7 is selected in accordance with the desired quantity of liquid to be dispensed. However, a change in the liquid throughput can also be obtained by raising or lowering the pressure of the liquid in the first line 1 while keeping the duration of opening of the closure device the same. During the period of opening of the solenoid the pressure maintaining valve 9 preferably closes so that there is no more recirculation of liquid. In particular, the volume of the first line and the delivery of the diaphragm pump 5 must be selected in relation to the quantity of liquid to be dispensed, so that if the solenoid 7 is opened there is no significant fall in the pressure of liquid in the first line 1. This is the case if the storage volume of the first line 1 is large enough in relation to the quantity of liquid dispensed in each case.

It is thus possible to dispense equal quantities of liquid at very short intervals of time with only a very slight range of fluctuations. With the additional division of the liquid into eight equal parts in the dispensing head 20, liquid can thus be dispensed into eight collecting containers in a single dispensing operation. This represents a significant speeding up of the dispensing process compared with the systems and apparatus known from the prior art. In addition, the dispensing process can easily be automated by process control as all the switching and conveying elements needed (solenoid, pressure maintaining valve and pump) are electrically operated or operate in the combined system without any external control signals.

Preferably, the dispenser 10 shown in FIG. 1 is arranged in a filling device. The dispensing of liquids from one or more storage containers 12 into one or more collecting containers is preferably done automatically, while in addition to the steps described above other steps may be partly or fully automated. Thus, the dispensing head 20 is preferably arranged in a parking/washing position at the start of a dispensing process. In another step, assuming that there are a plurality of storage containers available which are filled with liquid to be dispensed, one storage container is selected and one end of the second line and/or an aspirating needle mounted at the end of the second line are moved and positioned so that one end of the second line and/or the aspirating needle is or are immersed in the liquid.

In the case of a replaceable dispensing head, a dispensing head 20 suitable for the particular operation should be selected and connected to the solenoid by a line. Differences in the dispensing heads 20 may be the number of outlet openings or the diameter of the outlet openings or of the channels provided in the dispensing head. Moreover, if the dispensing head 20 is constructed to be moveable, it should be positioned so that it enables liquid to be dispensed into the collecting containers provided for this purpose. The dispensing head may be picked up by the gripper of a robot in order to position it. Alternatively or additionally however, it is also possible to bring the collecting containers into a suitable position for the dispensing process.

Then the pump which conveys the liquid is started up, at which stage the solenoid should be in its closed position. This is followed by a single or preferably repeated dispensing process as described above. In order to fill a plurality of collecting containers, e.g. microtitre plates, the collecting containers are preferably arranged in a matrix, in which the collecting containers in one row of the matrix are preferably filled simultaneously. Between the dispensing processes either the dispensing head 20 is moved so that a new row of collecting containers can be filled or the rows of collecting containers underneath the dispensing head 20 are moved so that in each dispensing process a new row is located underneath the dispensing head. When the dispensing process has ended the dispensing head 20 moves back into its parking/washing position.

Finally, the pipe system and the dispenser are conveniently washed to prevent any residues of a previous dispensing process remaining in the pipe system. A washing process is basically carried out in the same way as a dispensing process, using a washing liquid, e.g. deionized water, for the washing process. In order that the third line is also cleaned in addition to the main pipe system, the solenoid is preferably closed several times during the washing process. The washing liquid emerging from the dispensing head is caught by the parking/washing station and preferably discharged through a tube into a waste bottle.

The embodiment shown in FIG. 1 is particularly preferred. It makes it easier to rinse the apparatus when the liquid is changed and makes do with a small flushing volume.

Figure 2:
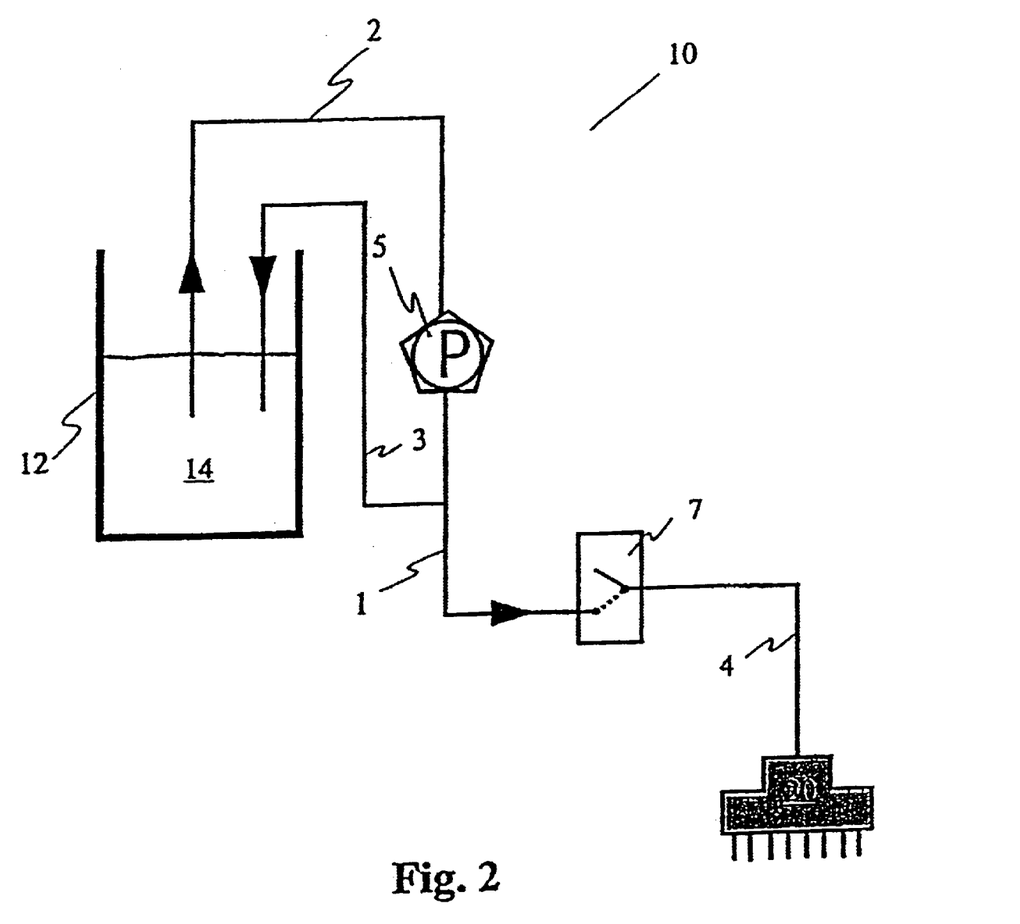
FIG. 2 a second dispenser constructed according to the invention in diagrammatic view.

FIG. 2 shows a second dispenser 10 according to the invention. Its construction differs from that of the dispenser in FIG. 1 particularly in the construction of the device for regulating the pressure of the liquid in the region between the diaphragm pump and the solenoid. The device for regulating the pressure of the liquid in the first line here comprises only a third line 3 which branches off the first line and opens into the storage element 12. In this device, which is simple in structure, the delivery of the diaphragm pump and the cross-section of flow of the third line have to be matched to one another so that a largely constant pressure prevails in the first line. Advantageously, for this purpose, the first line has a large volume.

Figure 3:
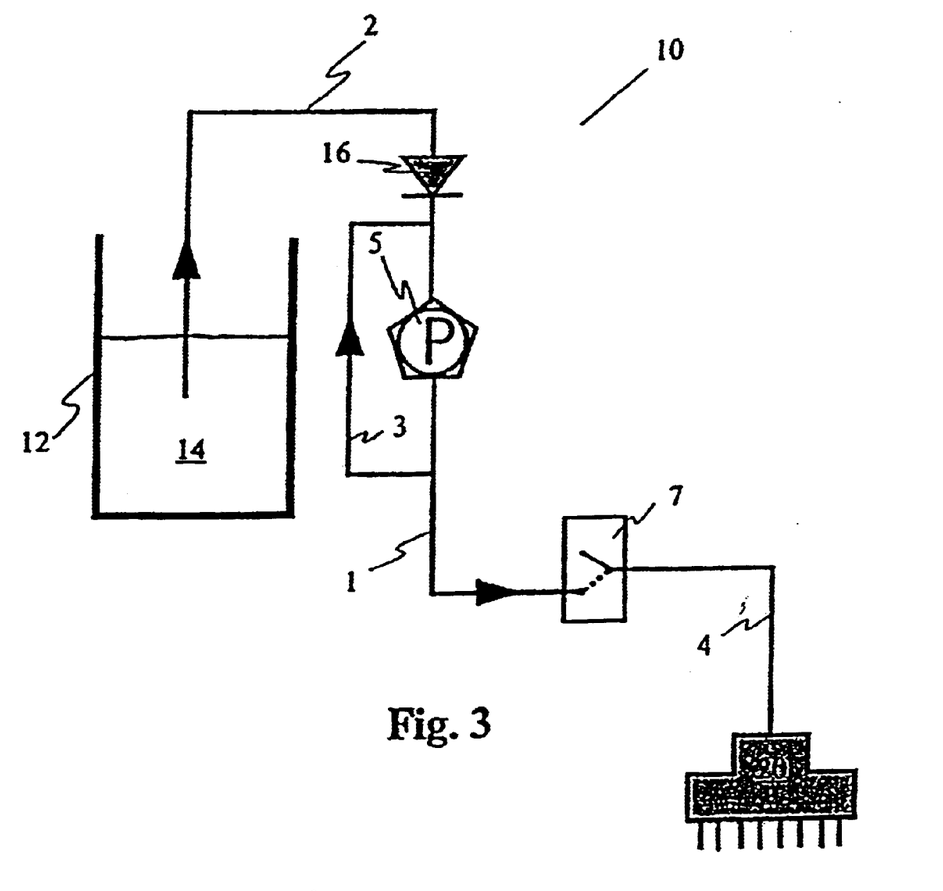
FIG. 3 a third dispenser constructed according to the invention in diagrammatic view.

A third dispenser according to the invention is shown in FIG. 3. The device for regulating the pressure of the liquid in the first line 1 here comprises a third line 3 and a non-return valve 16, the third line 3 branching off the first line 1 and opening into the second line 2, and moreover the non-return valve 16 is arranged in a region between the first end of the second line, closest to the storage element 12, and the point where the third line opens into the second line, as an intermediate element in the second line.

At this stage some or all of the quantity of liquid conveyed by the conveying element is recirculated, at least as long as the closure device is closed, while the liquid recirculating through the third line passes from the first line back into the second line. The non-return valve 16 prevents the recirculating liquid from flowing back into the storage element 12. However, because of the inherently closed recirculation circuit, the recirculating fluid may be heated up to some extent at high deliveries and low recirculation volumes. The non-return valve is optional but advantageous. Satisfactory results are obtained even without the non-return valve, but the use of a non-return valve can reduce the number of air bubbles in the line. This ensures greater accuracy.

Preferably, as shown in FIG. 3a, the line loop 3 is integrated in a solid block 8. This is most preferably connected immediately adjacent to or directly to the diaphragm pump. The closure device 7 (e.g. a solenoid) is conveniently attached directly to the loop block 8. Preferably the loop block and the closure device may be combined to form a valve block (not shown). The line 3 connects line 1 to line 2 as a transverse channel within the loop block. The optional but advantageous non-return valve is conveniently arranged in the loop block in the area where the line 2 enters the loop block.

Figure 4:
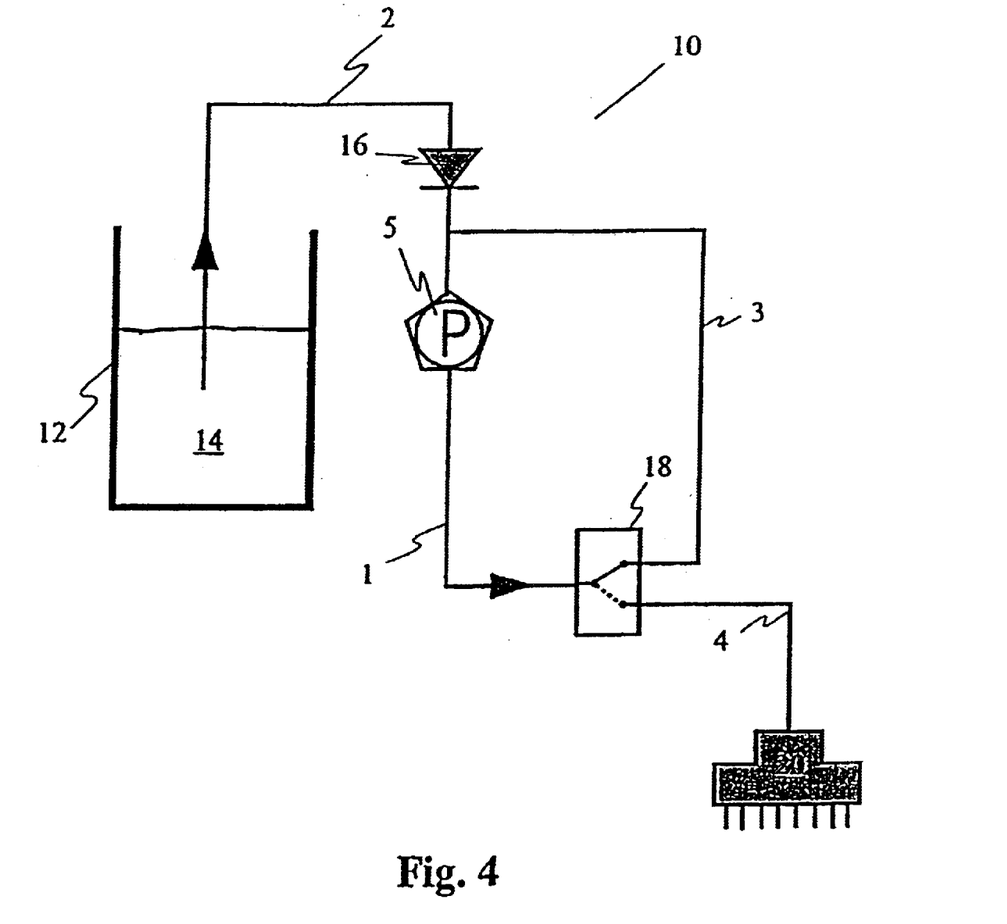
FIG. 4 a fourth dispenser constructed according to the invention in diagrammatic view.

In another preferred embodiment of the device for regulating the pressure of the liquid in the first line 1 the solenoid 18 is constructed as a 3/2-way solenoid as shown in FIG. 4 and the device for regulating the pressure of the liquid in the first line further comprises a third line 3 and a non-return valve 16, the third line connecting one of the two outlets of the 3/2-way solenoid to the second line and moreover the non-return valve is arranged as an intermediate element in the second line in a region between the first end of the second line and the point where the third line opens into the second line. By means of the 3/2-way solenoid the liquid is able to circulate in the first and third lines when the closure device is closed in the waiting position. Here again the non-return valve is optional but advantageous. Even without a non-return valve satisfactory results are obtained but the use of a non-return valve can reduce the number of air bubbles in the line, leading to greater accuracy.

Preferably, the first line and/or the second line and/or the third line of the dispensing device consists of an easily bendable plastic, which has resistance to the liquid which is to be dispensed. Alternatively, it is also expedient to use lines made of silicon.

The dispensing pump and also the solenoid are preferably supplied with 24 volt d.c. current. As a result, even in the event of an electrical short circuit, there is no danger to any operator coming into contact with the device.

Figure 5:
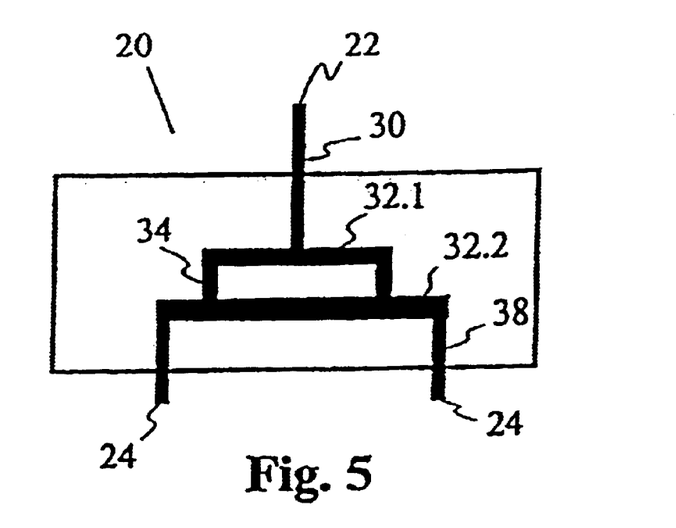
FIG. 5 a longitudinal section through a dispensing head constructed according to the invention with an inlet opening and two outlet openings.

FIG. 5 shows a dispenser head 20 constructed according to the invention with an inlet opening 22 and two outlet openings 24. The liquid to be dispensed passes through the inlet opening 22 into the inlet channel 30 of the dispenser head 20. At the end of the inlet channel 30 this latter opens into a first pressure stage constructed as a first transverse channel 32.1. In this pressure stage the liquid is distributed through the first transverse channel 32.1 perpendicularly to the inlet channel. The transverse channel 32.1 is preferably larger in diameter than the inlet channel 30 which opens into it. Moreover, the diameter of the first transverse channel 32.1 is preferably larger than the diameter of the supply channels 34 leading away from the first transverse channel. Both aspects help to ensure that the first transverse channel 32.1 is uniformly filled over its full extent with liquid to be dispensed before the liquid is conveyed onwards.

Two supply channels 34, each provided at both ends of the first transverse channel 32.1, then carry the liquid into a second transverse channel 32.2. The supply channels 34 preferably lead off from the first transverse channel 32.1 perpendicularly thereto, in the embodiment shown, and rejoin the second transverse channel 32.2, again preferably at right angles thereto. The perpendicular arrangement of the channels ensures that the channels are filled step by step; in addition, a perpendicular arrangement is easier to achieve in the manufacturing process. From the second pressure stage which is in turn constructed as a transverse channel 32.2, the liquid is conveyed into the entry area of the outlet channels 38. In the embodiment shown the two outlet channels 38 are arranged at the opposite ends of the second transverse channel. Since the supply channels 34 open into the second transverse channel 32.1 further inwards, the liquid has to migrate towards the outer ends of the second transverse channel 32.1 to reach the particular outlet channel 34. The diameter of the second transverse channel 32.2 is in turn preferably greater than the diameter of the supply channels 34 and/or the outlet channels 38. The liquid travelling from the supply channels 34 into the second transverse channel 32.2 can easily spread out in this pressure stage before the associated outlet channels 38 are filled with the liquid.

In the embodiment of the dispenser head shown, having two outlet channels, a section which is not regularly flushed with liquid may form in the region of the second transverse channel 32.2 located between the two supply channels. The volumes of liquid contained in this section have a tendency to stay longer in the dispenser head 20. In some circumstances this may mean that in spite a number of dispensing operations carried out sequentially, residual amounts of the liquid originally held in this section will still be found there. In the worst case, even when the liquid is changed or the liquid to be dispensed is expelled with a wash solution, residues may be left behind in this section which will then be successively dispensed with other liquids in successive dispensing operations, contaminating these other liquids. This problem can be reduced by moving the outlet channels inwards. In a preferred embodiment of this kind the outlet channels 38 are located in the section of the second transverse channel 32.2 located between the supply channels 34 (not shown).

At the lower end of the outlet channels the liquid to be dispensed is released through the outlet openings 24. The outlet openings may end flush with the underside of the dispenser head (not shown) or may lead out of the dispenser head 20 by means of a continuation of the outlet channel, e.g. in the form of a hollow cylinder or a needle. In these preferred embodiments it is easier to dispense the liquid into containers in a controlled manner.

FIG. 5 shows a vertical longitudinal section through the dispenser head 20. In the embodiment shown the two transverse channels are arranged vertically one above the other. This is one of a number of possible arrangements and is not obligatory. Preferably, the two pressure stages are arranged in a horizontal plane or the first pressure stage is arranged underneath the second pressure stage to promote successive filling of the individual channel stages.

Figure 6A:
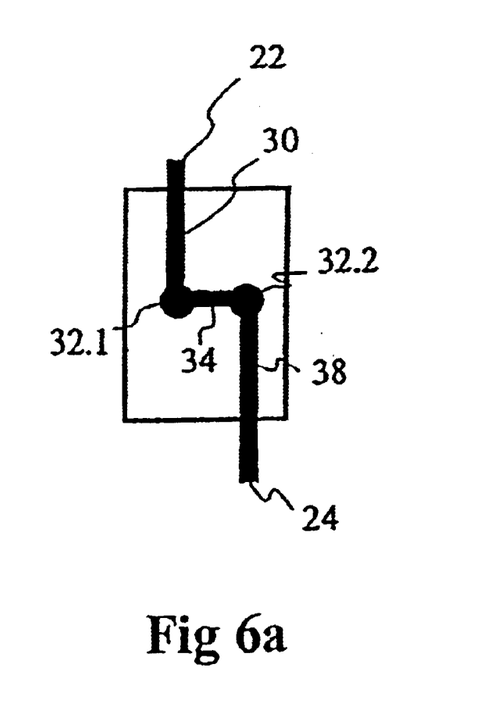
FIG. 6a a cross-section through a dispenser head according to the invention with two transverse channels on one level.

FIG. 6*a* shows a vertical cross-section through a dispenser head. In this representation the number of outlet openings is not shown and is irrelevant to the following discussion. In the dispenser head 20 the liquid to be dispensed is fed through the inlet opening 22 into the inlet channel 30 and conveyed vertically downwards. There it enters the first pressure stage which is formed by a first transverse channel 32.1, which has a larger diameter than the inlet channel. Supply channels lead horizontally off the first transverse channel 32.1. These supply channels in turn are smaller in diameter than the first transverse channel 32.1. The liquid passing through the inlet channel 30 into the first transverse channel fills the latter with liquid, at least in the lower region, initially over its complete length before the liquid enters the individual supply channels. Thus, pressure is equalised over the entire pressure stage of the first transverse channel and all the supply channels are acted upon by approximately the same liquid pressure from the liquid which is to be dispensed.

The liquid passes through the supply channels 34 into the second pressure stage. Here again, the second pressure stage is constructed as a transverse channel 32.2 of fairly large diameter. Depending on the diameter of the outlet channels proceeding from the second transverse channel and their resistance coefficient, the second pressure stage is filled more or less completely before the liquid enters the outlet channels 38. In this way a uniform pressure profile prevailing at the inlet regions of the outlet channels is obtained and the liquid is evenly dispensed.

Figure 6B:
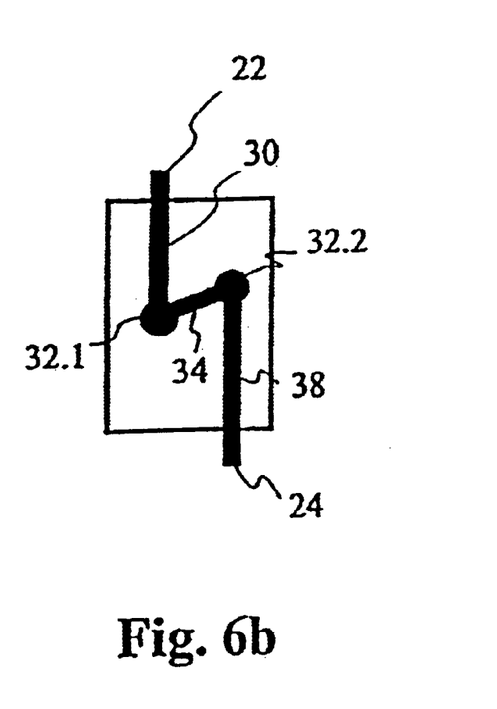
FIG. 6b a cross-section through a dispenser head constructed according to the invention with a first transverse channel underneath a second transverse channel.

In FIG. 6b the first pressure stage comes to lie below the second pressure stage. If the lowest point of the area where the supply channels 34 enter the second transverse channel 32.2 is higher than the highest point of the first transverse channel 32.1 this ensures that the first transverse channel will be completely filled before the liquid enters the second transverse channel. This in turn requires uniform filling of the second transverse channel and results in minor differences in the release of liquid from the individual outlet channels 38.

The pressure stages shown in FIGS. 6a and 6b are constructed as transverse channels arranged perpendicularly to the channels connected thereto. The transverse channels themselves are constructed as cylindrical bores. Basically, the pressure stages may also be differently shaped. For example, it is possible to have rectangular or oval cross-sections varying over their longitudinal extent. In addition, the individual channels may also open diagonally into one another. However, the perpendicular arrangement of the individual channel steps and the construction of the individual channels as cyclindrical bores is preferred.

Figure 7:
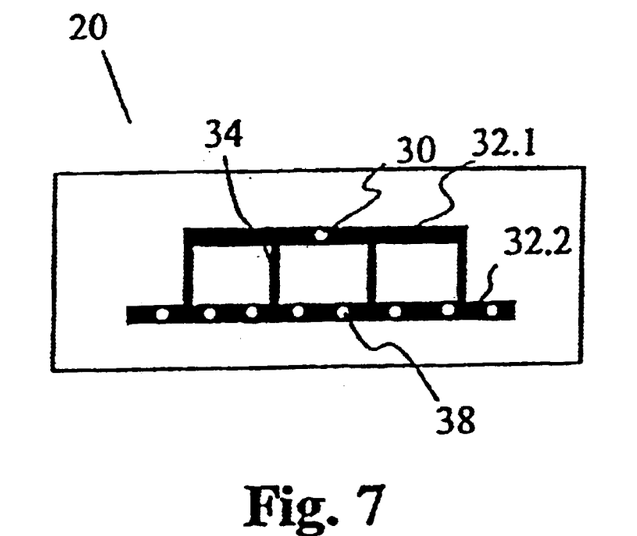
FIG. 7 a longitudinal section through a dispensing head constructed according to the invention with one inlet opening and eight outlet openings.

FIG. 7 shows a preferred dispensing head according to the invention particularly for use in a dispenser according to the invention. The dispensing head has an inlet opening and eight outlet openings, the inlet opening being connected to the outlet openings by means of channels provided in the dispensing element. The channel runs from the inlet opening to the outlet openings in such a way that the inlet channel 30 which is connected to the inlet opening in the dispensing element initially branches into four second channels which in turn branch into two third channels, each of the third channels being connected to one outlet opening.

The points where the channels branch in their associated branching plane communicate with one another. To ensure even distribution of the liquid flowing in through the inlet opening the flow channels should be constructed so that the flow resistance along the channels is the same between the inlet opening and each of the eight outlet openings. This may be achieved by having the cross-sections of the channels varying locally or over the entire length of the channel in such a way that the throttle effect is the same in each case from the inlet opening to each of the outlet openings. Channels designed in this way thus have the same flow resistances for liquids within a wide range of viscosities, with the result that the liquid flowing in through the inlet opening into the dispensing head is distributed equally over the outlet openings.

In the dispenser head shown in FIG. 7 the two pressure stages are constructed as transverse channels 32.1 and 32.2 and take the form of cylindrical bores. The inlet channel opens perpendicularly into the first transverse channel and supplies it with liquid. The diameter of the first transverse channel 32.1 is greater than the diameter of the inlet channel 30 directly connected thereto and the diameters of the supply channels 34 directly connected thereto. As shown in the horizontal section through the dispenser head, the first transverse channel is located horizontally on the same plane or lower than the second transverse channel. The four supply channels are distributed symmetrically along the length of the first transverse channel and supply the second transverse channel. To the left and right of each point where a supply channel opens into the second transverse channel 32.2 there is an outlet channel, so that an individual supply channel primarily supplies two outlet channels with liquid.

The two outermost outlet channels are located in the end region of the second transverse channel which is in the form of a blind bore at this point. In these areas, liquid residues may accumulate, which are not flushed out. To avoid this, the blind space at the ends of the second transverse channel are preferably reduced so that the ends of the second transverse channel merge precisely into the outer outlet channels (not shown).

In a preferred production method the channels to be arranged in the dispenser head are drilled from the outside. This produces either a blind bore which can then be closed off again, with the exception of the inlet channel and outlet channels, or a through-bore in which case both ends have to be sealed afterwards, with the above exceptions. Care must be taken to ensure that no residues which will have a negative effect on the flow, e.g. sharp burrs or the like, are left behind in the channel system.

Figure 8:
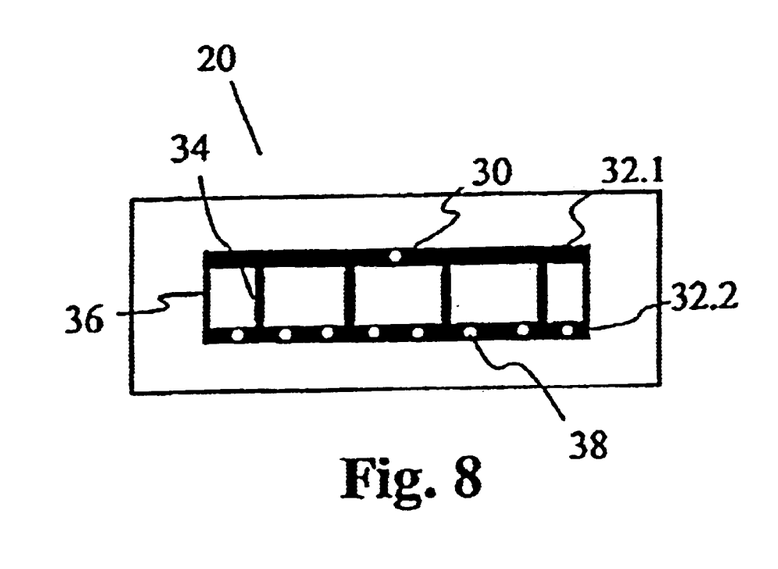
FIG. 8 a longitudinal section through a dispensing head constructed according to the invention with one inlet opening and eight outlet openings according to FIG. 7 as well as two flushing channels.

FIG. 8 shows a particularly preferred embodiment of the dispenser head 20 with an inlet opening and eight outlet openings. In contrast to the dispenser head according to FIG. 7, the dispenser head 20 shown in FIG. 8 has two additional flushing channels 36 which connect the first and second transverse channel (pressure stages) to one another. The first transverse channel is longer in relation to other embodiments and merges into the flushing channels 36 at its two outer ends. The flushing channels then supply the second transverse channel and its outer ends. This arrangement ensures that there is no room for liquids to accumulate and/or for bubbles to form at the ends of the transverse channels. The flushing channels serve to circulate the liquid in this part of the dispenser.

The diameter of the flushing channels 36 is preferably less than the diameter of the supply channels 34. The outlet channels located furthest out are supplied with liquid by both the last supply channel and by the flushing channel. By reducing the diameter of the flushing channel 36 an excessive throughput of liquid through the outlet channels at the edge is avoided.

Figure 9:
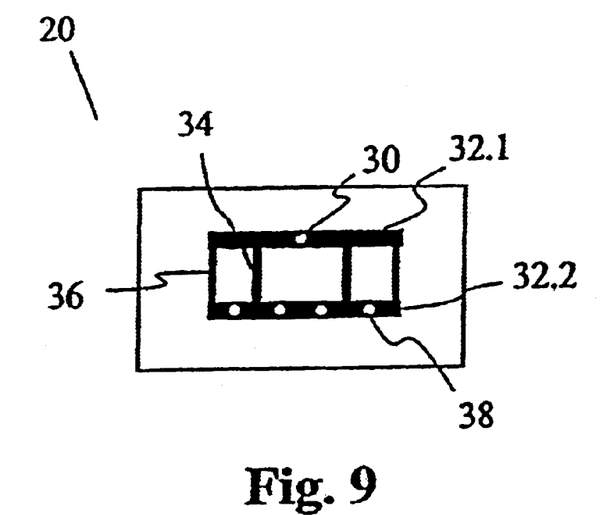
FIG. 9 a longitudinal section through a dispensing head constructed according to the invention with one inlet opening and four outlet openings.
Figure 10:
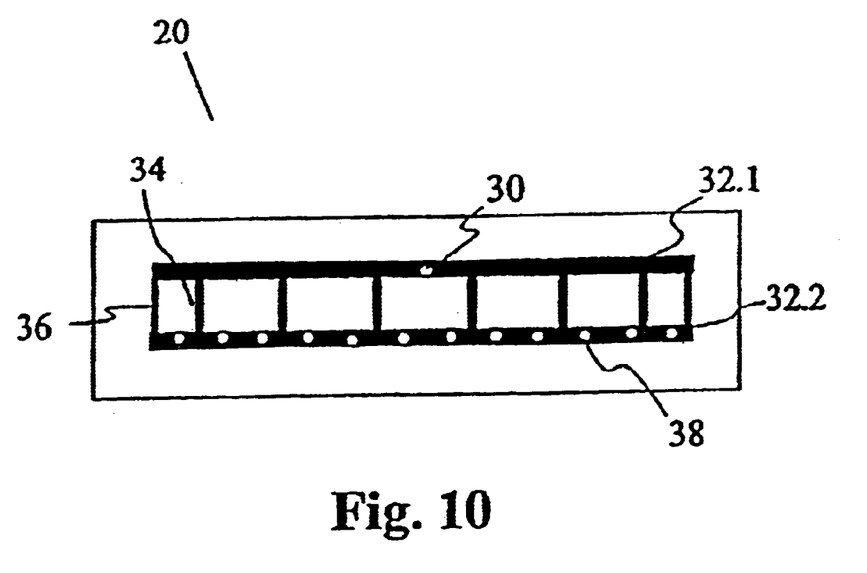
FIG. 10 a longitudinal section through a dispensing head constructed according to the invention with one inlet opening and twelve outlet openings.

FIG. 9 shows a horizontal section through the dispenser head 20 with one inlet channel and four outlet channels. As in FIG. 8 the two pressure stages are joined together by additional flushing channels. In the drawings, functionally similar features have been given the same reference numerals. FIG. 10 shows a horizontal section through a dispenser head with an inlet channel 30 and twelve outlet channels 38. The construction of this dispenser head is a systematic further development of the corresponding 4-fold and 8-fold dispenser heads shown in FIGS. 9 and 8. Of course, the 12-fold dispenser head may also be manufactured without flushing channels but the use of flushing channels is beneficial. A dispenser head with ten outlet channels may be manufactured omitting the two outer flushing channels and the two outer outlet channels. The sizes of the supply channels which are now on the outside are determined empirically. However, the preferred embodiment is the dispenser head shown in FIG. 8 with one inlet channel and eight outlet channels.

Figure 11:
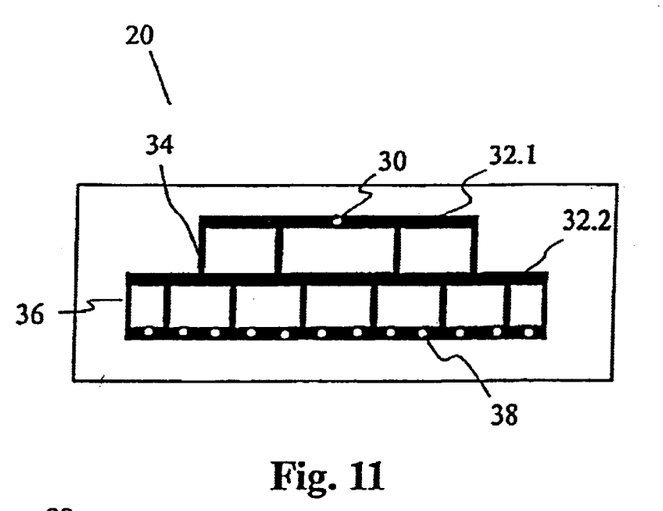
FIG. 11 a longitudinal section through a dispensing head constructed according to the invention with one inlet opening and twelve outlet openings, and with three transverse channels.

A three-stage dispenser head 20 with twelve outlet channels is shown in FIG. 11. The horizontal section through the dispenser head indicates that all three pressure stages extend substantially in the same horizontal plane. It is also advantageous here to incorporate a slope, from the first pressure stage to the third pressure stage, to achieve step by step filling of the individual pressure reservoirs. The additional use of another pressure stage ensures higher precision in the delivery of the individual volumes of liquid through the relevant outlet channels. However, the larger total volume of liquid stored in the dispenser head, compared with the two-stage dispenser head, is a disadvantage as all of this has to be discarded as waste when the liquid is changed. The pressure stage is connected to the second pressure stage by means of four supply channels; the second pressure stage is connected to the third pressure stage by means of six supply channels and two flushing channels. The number of supply and flushing channels provided between the individual pressure stages is not rigidly prescribed. Variations on the version shown in FIG. 11 are possible without departing from the underlying inventive concept.

Figure 12A:
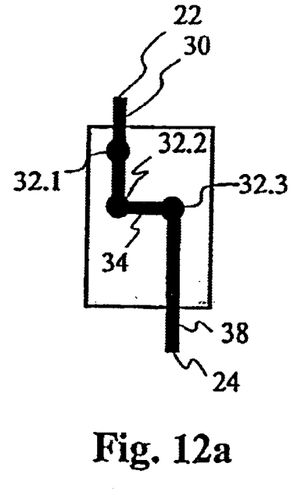
FIG. 12a a vertical cross-section through a dispensing head according to the invention with three transverse channels.
Figures 12B, 12C:
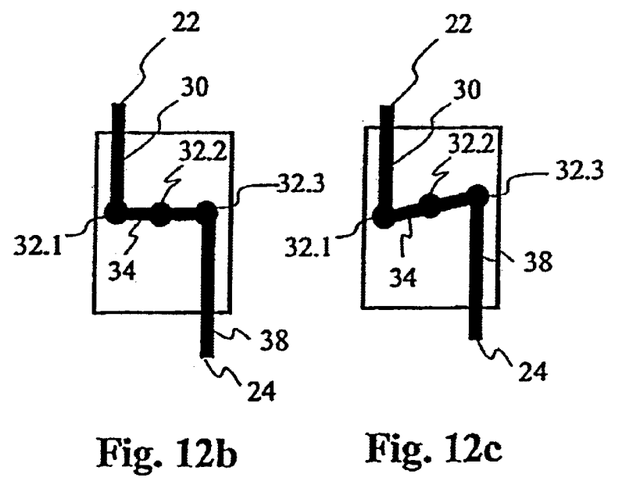
FIG. 12b a vertical cross-section through a dispensing head according to the invention with three horizontally arranged transverse channels.
FIG. 12c a vertical cross-section through a dispensing head according to the invention with three ascending transverse channels.

FIGS. 12a, 12b and 12c show vertical cross-sections through three-stage dispenser heads. In FIG. 12a the first two pressure stages are arranged vertically one above the other while the third pressure stage is located horizontally on the same plane as the second pressure stage. In FIG. 12b all three pressure stages are located on the same horizontal plane whereas in FIG. 12c the three pressure stages have a gradient, starting from the first pressure stage, with the third pressure stage highest. In these embodiments of the dispenser heads the pressure stages are preferably in the form of bores which preferably have a larger diameter than the channels immediately adjacent to them.

Basically, in the dispenser heads, the intention is to arrange the pressure stages and channels symmetrically to achieve a precise delivery of accurately defined volumes of liquid through the individual outlet openings. It is also possible to provide the dispenser heads with more than one inlet opening. The usefulness of such an embodiment may be apparent with a larger number of outlet openings.

In another preferred embodiment of the dispensing head, pipetting needles (not shown) are arranged in one or more outlet channels. The pipetting needles are constructed here as capillary tubes, preferably made of glass and are introduced into the particular outlet channel in a first partial section. The capillary tubes also project out of the outlet openings to some extent.

The capillary tubes have an internal and external diameter. The outlet channels are constructed in their first section with a diameter of opening which corresponds to the external diameter of the capillary tubes and in a second section, immediately adjacent the first section, they have a diameter of opening which corresponds to the internal diameter of the capillary tubes, so that the capillary tubes are held in the third channels on the one hand by fitting tightly therein and on the other hand the transition for the liquid flowing through the dispensing element out of the outlet channels 38 into the capillary tube is smooth. Thanks to the shape of the internal diameter of these pipetting needles it is thus possible to achieve fine adjustment of the flow resistance along a distribution channel by for example selecting a channel which narrows inside the pipetting needle.

List of Reference Numerals 1 first line
2 second line
3 third line
4 fourth line
5 pump (diaphragm pump)
7 valve (solenoid) 2/2-way valve
8 loop block
9 pressure maintaining valve
10 dispenser
12 storage element (buffer bottle)
14 liquid
16 nonreturn valve
18 valve (solenoid) 3/2-way valve
20 dispenser head
22 inlet opening
24 outlet opening
30 inlet channel
32.1 first transverse channel
32.2 second transverse channel
32.2 third transverse channel
34 supply channel
36 flushing channel
38 outlet channel

What we claimed is:

1. A dispenser for the substantially automated and finely metered dispensing of liquids, the dispenser comprising:
   a first line;
   a conveying element for conveying the liquid which is to be dispensed through the first line, wherein the liquid is transported out of the storage element by the conveying element and conveyed into the first line, wherein the conveying element is connected to the storage element by means of a second line and the end of the second line proximal to the storage element is movable in the direction of the immersion in the liquid in the storage element;
   a closure device for the rapid closing and rapid opening of the first line, the closure device being located downstream of the conveying element in the direction of travel of the liquid;
   a device for regulating the pressure of the liquid in the area between the conveying element and the closure device, the device comprising a third line which branches off the first line, as well as a pressure valve for opening and closing the third line, wherein the third line opens into the second line upstream of the conveying element in the direction of travel of the liquid.

2. The dispenser according to claim 1, wherein the conveying element is a pump.

3. The dispenser according to claim 2, wherein the pump is a diaphragm pump.

4. The dispenser according to claim 1, further comprising an aspiration needle on the end of the second line proximal to the storage element.

5. The dispenser according to claim 4, wherein a liquid sensor for determining and regulating the depth of immersion in the liquid of the storage element is provided on the end of the second line proximal to the storage element.

6. The dispenser according to claim 5, wherein the end of the second line proximal to the storage element is automatically movable to another storage element or the storage element is automatically replaceable by another storage element.

7. The dispenser according to claim 6, wherein the pressure of the liquid in the region between the conveying element and the closure device is regulated, by means of the device for regulating the pressure, so as not to exceed a threshold value.

8. The dispenser according to claim 7, wherein a dispensing element with at least one inlet opening and at least one outlet opening is provided on the end of the first line downstream of the conveying element.

9. The dispenser according to claim 8, wherein the dispensing element is constructed as a dispensing head with automated movement.

10. The dispenser according to claim 8, wherein the dispensing element is automatically replaceable.

11. The dispenser according to claim 10, wherein the direction of conveying of the conveying element is reversible.

12. The dispenser according to claim 1, wherein the opening and closing cycle of the closing device can be controlled by a microprocessor.

13. The dispenser according to claim 12, wherein the lines are made from a plastic that is easily bendable.

14. The dispenser according to claim 13, wherein the dispensing element dispenses the liquid into one or more collecting containers.

15. The dispenser according to claim 14, wherein the dispensing element further comprises an inlet opening and at least two outlet openings; a first and a second transverse channel for distributing the liquid which is to be dispensed; and at least two supply channels between the first and second transverse channels.

16. The dispenser according to claim 15, wherein the dispensing element has eight outlet openings.

17. The dispenser according to claim 15, wherein the dispenser has twelve outlet openings.

18. The dispenser according claim 15, wherein an inlet channel downstream of the inlet opening runs substantially perpendicularly to the first transverse channel.

19. The dispenser according to claim 18, wherein the supply channels run substantially perpendicularly to the first and second transverse channels.

20. The dispenser according to claim 19, wherein outlet channels leading to the outlet openings run substantially perpendicularly to the second transverse channel.

21. The dispenser according to claim 20, wherein the first transverse channel extends on the same level as the second transverse channel.

22. The dispenser according to claim 20, wherein the first transverse channel extends underneath the second transverse channel.

23. The dispenser according to claim 22, wherein the supply channels supply outlet openings with liquid to be dispensed, wherein two outlet openings are provided for each supply channel.

24. The dispenser according to claim 23, wherein the transverse channels are connected by additional flushing channels.

25. The dispenser according to claim 24, wherein additional transverse channels are provided.

26. The dispenser according to claim 25, wherein the diameter of the flushing channels is smaller than the diameter of the supply channels.

27. The dispenser according to claim 26, wherein the diameter of the supply channels is less than the diameter of the transverse channels.

28. The dispenser according to claim 27, wherein the flow resistance along the channels between the inlet opening and the outlet openings is substantially equal.

29. The dispenser according to claim 28, wherein the dispensing element further comprises
   an inlet opening and at least two outlet openings;
   a first and a second pressure stage for equalizing the pressure within the pressure stage in question; and
   at least two supply channels between the two pressure stages.

30. The dispenser according to claim 1, wherein the closure device is a solenoid.

31. A process for the substantially automated, finely metered dispensing of liquids, the process comprising the following steps:
   a) automatically moving one end of a pipe system so that the pipe system communicates with a selected storage container;
   b) transporting the liquid out of the storage container into the pipe system;
   c) building up a pressure which is substantially constant over time in the liquid in at least one section of the pipe system, wherein the liquid is continuously conveyed by means of a pump in order to build up the pressure, and wherein the pressure is limited on the pump delivery side by recycling of the liquid; and
   d) metering the quantity of liquid to be dispensed by briefly opening a rapid closure device arranged in the pipe system, so that a quantity of liquid corresponding to the duration of opening of the rapid closure device and the liquid pressure is dispensed from the section of the pipe system.

32. The process according to claim 31, wherein step c) of the process further comprises the step of limiting the pressure on the pump delivery side by pressure-controlled recycling of the liquid.

33. The process according to claim 32, wherein step c) of the process is repeated several times in succession.

34. The process according to claim 33, wherein before step c) of the process the distal end of the pipe system in relation to the storage element is automatically moved so that the metered quantity of liquid is dispensed into one or more selected containers.

35. The process according to claim 31, wherein the containers into which the metered liquid is dispensed are moved in a controlled manner before step c) of the process.

36. The process according to claim 31, wherein when a maximum pressure is exceeded in the pipe system the liquid is recycled into the storage element.

37. The process according to claim 31, wherein when a maximum pressure is exceeded in the pipe system the liquid is recycled into a part of the pipe system situated in front of the pump.

38. The process according to claim 31, wherein after the end of the dispensing of the liquid the pipe system is washed with a washing liquid.

* * * * *